US 12,377,251 B2

(12) United States Patent
Levy et al.

(10) Patent No.: US 12,377,251 B2
(45) Date of Patent: *Aug. 5, 2025

(54) APPARATUS AND METHOD FOR PRODUCING AN ENRICHED MEDICAL SUSPENSION OF CARBON DIOXIDE

(71) Applicants: Frank Levy, Fort Myers, FL (US); Kimberley Levy, Fort Myers, FL (US)

(72) Inventors: Frank Levy, Fort Myers, FL (US); Kimberley Levy, Fort Myers, FL (US)

( * ) Notice: Subject to any disclaimer, the term of this patent is extended or adjusted under 35 U.S.C. 154(b) by 110 days.

This patent is subject to a terminal disclaimer.

(21) Appl. No.: 18/312,217

(22) Filed: May 4, 2023

(65) Prior Publication Data

US 2023/0310820 A1 Oct. 5, 2023

Related U.S. Application Data

(63) Continuation of application No. 16/424,616, filed on May 29, 2019, now Pat. No. 11,679,244, which is a
(Continued)

(51) Int. Cl.
*A61M 35/00* (2006.01)
*A01N 25/00* (2006.01)
(Continued)

(52) U.S. Cl.
CPC .......... *A61M 35/003* (2013.01); *A01N 25/00* (2013.01); *A61K 9/122* (2013.01); *A61M 5/2053* (2013.01);
(Continued)

(58) Field of Classification Search
CPC ............ A61M 25/003; A61M 25/0028; A61M 25/026; A61M 3/005; A61M 16/12;
(Continued)

(56) References Cited

U.S. PATENT DOCUMENTS 2,475,511 A 7/1949 Nicholson
2,688,428 A 9/1954 Manhartsberger
(Continued)

FOREIGN PATENT DOCUMENTS

CN 2179152 Y 10/1994
DE 10151027 A1 6/2003
(Continued)

*Primary Examiner* — Scott J Medway
*Assistant Examiner* — Anh Bui
(74) *Attorney, Agent, or Firm* — Welsh Flaxman & Gitler LLC

(57) ABSTRACT

A medical fluid suspension generating apparatus for performing medical procedures includes a Venturi-agitating tip assembly composed of a multi-channel arrangement at a proximal first end thereof and a tip at a distal second end thereof. The apparatus also includes a compressed medical fluid unit fluidly connected to the multi-channel arrangement at a proximal first end of the Venturi-agitating tip assembly and a medical solution fluidly connected to the multi-channel arrangement at a proximal first end of the Venturi-agitating tip assembly. Pressurized gas, from the compressed medical fluid unit, and the medical solution are combined within the Venturi-agitating tip assembly in a manner generating an enriched medical suspension that is ultimately dispensed from the suspension delivery apparatus.

1 Claim, 11 Drawing Sheets

Related U.S. Application Data continuation of application No. 15/696,772, filed on Sep. 6, 2017, now Pat. No. 10,350,399, which is a continuation-in-part of application No. 15/053,530, filed on Feb. 25, 2016, now Pat. No. 10,155,093, which is a continuation-in-part of application No. 14/509,459, filed on Oct. 8, 2014, now Pat. No. 9,744,342, which is a continuation of application No. 13/068,680, filed on May 17, 2011, now Pat. No. 8,876,749, which is a continuation-in-part of application No. 12/652,845, filed on Jan. 6, 2010, now abandoned, which is a continuation-in-part of application No. 12/210,368, filed on Sep. 15, 2008, now abandoned, which is a continuation-in-part of application No. 11/945,674, filed on Nov. 27, 2007, now Pat. No. 7,543,760.

(60) Provisional application No. 62/121,827, filed on Feb. 27, 2015, provisional application No. 60/867,323, filed on Nov. 27, 2006.

(51) Int. Cl.

| | | |
|---|---|---|
| *A61K 9/12* | (2006.01) | |
| *A61M 5/20* | (2006.01) | |
| *A61M 13/00* | (2006.01) | |
| *A61M 37/00* | (2006.01) | |
| *A61B 17/00* | (2006.01) | |
| *A61B 17/12* | (2006.01) | |
| *A61K 9/00* | (2006.01) | |
| *A61M 5/00* | (2006.01) | |
| *A61M 25/00* | (2006.01) | |
| *B05B 7/04* | (2006.01) | |
| *B05B 7/24* | (2006.01) | |

(52) U.S. Cl.
CPC .......... *A61M 13/003* (2013.01); *A61M 35/00* (2013.01); *A61M 37/00* (2013.01); *A61B 2017/00884* (2013.01); *A61B 2017/00893* (2013.01); *A61B 2017/1205* (2013.01); *A61B 17/12186* (2013.01); *A61K 9/0019* (2013.01); *A61K 9/124* (2013.01); *A61M 2005/006* (2013.01); *A61M 25/0026* (2013.01); *A61M 2202/0225* (2013.01); *B05B 7/0483* (2013.01); *B05B 7/2421* (2013.01); *B05B 7/2424* (2013.01)

(58) Field of Classification Search
CPC ........ A61M 16/127; A61M 2202/0225; A61M 2005/006; A61M 37/00; A61M 35/00; A61M 35/003; A61M 13/003; A61M 5/2053; A61K 9/124; A61K 9/122; A61K 9/0019; A61B 2017/1205; A61B 2017/00893; A61B 2017/00884; A61B 17/12186
See application file for complete search history.

(56) References Cited

U.S. PATENT DOCUMENTS

| | | | |
|---|---|---|---|
| 2,828,889 | A | 4/1958 | Joschko |
| 3,004,686 | A | 10/1961 | McKee |
| 3,034,332 | A | 5/1962 | Lederer |
| 3,831,844 | A | 8/1974 | Tropeano et al. |
| 3,879,703 | A | 4/1975 | Bonazoli et al. |
| 4,189,068 | A | 2/1980 | Apellaniz |
| 4,219,021 | A | 8/1980 | Fink |
| 4,744,356 | A | 5/1988 | Greenwood |
| 4,786,394 | A | 11/1988 | Enzer et al. |
| 4,950,230 | A | 8/1990 | Kendell |
| 5,135,026 | A | 8/1992 | Manska |
| 5,154,348 | A | 10/1992 | Ratnik et al. |
| 5,195,963 | A | 3/1993 | Yafuso et al. |
| 5,246,140 | A | 9/1993 | Thix et al. |
| 5,345,932 | A | 9/1994 | Yafuso et al. |
| 5,395,318 | A | 3/1995 | Kaprelian |
| 5,580,530 | A | 12/1996 | Kowatsch et al. |
| 5,699,961 | A | 12/1997 | Ratnik et al. |
| 5,875,776 | A | 3/1999 | Vaghefi |
| 5,964,223 | A | 10/1999 | Baran |
| 6,164,556 | A | 12/2000 | Dupre et al. |
| 6,192,883 | B1 | 2/2001 | Miller, Jr. |
| 6,295,007 | B1 | 9/2001 | O'Meara |
| 6,315,762 | B1 | 11/2001 | Recinella et al. |
| 6,378,570 | B1 | 4/2002 | Shipachev et al. |
| 6,402,047 | B1 | 6/2002 | Thomas |
| 6,474,091 | B2 | 11/2002 | Guerra |
| 6,572,873 | B1 | 6/2003 | Osman et al. |
| 6,959,708 | B1 | 11/2005 | Rasor et al. |
| 7,543,760 | B2 | 6/2009 | Levy et al. |
| 8,876,749 | B2 | 11/2014 | Levy |
| 9,744,342 | B2 | 8/2017 | Levy |
| 10,155,093 | B2 | 12/2018 | Levy et al. |
| 10,322,271 | B2 | 6/2019 | Levy et al. |
| 10,350,398 | B2 | 7/2019 | Levy |
| 10,350,399 | B2 * | 7/2019 | Levy ...................... A01N 25/00 |
| 11,185,671 | B2 | 11/2021 | Levy et al. |
| 11,679,244 | B2 * | 6/2023 | Levy ................... A61M 5/2053 |
| | | | 604/24 |
| 11,690,988 | B2 | 7/2023 | Levy et al. |
| 2001/0044618 | A1 | 11/2001 | Recinella et al. |
| 2002/0017328 | A1 | 2/2002 | Loo |
| 2002/0174578 | A1 | 11/2002 | Ross |
| 2003/0181850 | A1 | 9/2003 | Diamond et al. |
| 2005/0000981 | A1 | 1/2005 | Peng et al. |
| 2005/0092315 | A1 | 5/2005 | Bachelder |
| 2005/0103342 | A1 | 5/2005 | Jorczak et al. |
| 2005/0119607 | A1 | 6/2005 | Van Der Linden et al. |
| 2006/0004322 | A1 | 1/2006 | Uesugi et al. |
| 2006/0071091 | A1 | 4/2006 | Ratnik |
| 2006/0074386 | A1 | 4/2006 | Wollmann |
| 2006/0178620 | A1 | 8/2006 | Wollmann et al. |
| 2007/0104616 | A1 | 5/2007 | Keenan et al. |
| 2007/0104651 | A1 | 5/2007 | Wright et al. |
| 2007/0111298 | A1 | 5/2007 | Muller et al. |
| 2007/0244429 | A1 | 10/2007 | Nguyen et al. |
| 2008/0004549 | A1 | 1/2008 | Anderson et al. |
| 2008/0120992 | A1 | 5/2008 | Levy et al. |
| 2008/0167621 | A1 | 7/2008 | Wagner et al. |
| 2009/0062741 | A1 | 3/2009 | Smith et al. |
| 2009/0318890 | A1 | 12/2009 | Levy |
| 2010/0101579 | A1 | 4/2010 | Levy |
| 2010/0152880 | A1 * | 6/2010 | Boyden .................. A61K 38/38 |
| | | | 700/283 |
| 2011/0112041 | A1 | 5/2011 | Schiffmann |
| 2011/0218411 | A1 | 9/2011 | Keenan et al. |
| 2012/0305669 | A1 | 12/2012 | Meron et al. |
| 2017/0153165 | A1 * | 6/2017 | Nwadigo .............. B01L 3/0231 |

FOREIGN PATENT DOCUMENTS

| | | |
|---|---|---|
| EP | 2468204 A1 | 6/2012 |
| EP | 2548607 A2 | 1/2013 |
| WO | 9300951 A1 | 1/1993 |
| WO | 0072821 A1 | 12/2000 |
| WO | 0241872 A1 | 5/2002 |
| WO | 2005048984 A1 | 6/2005 |

\* cited by examiner

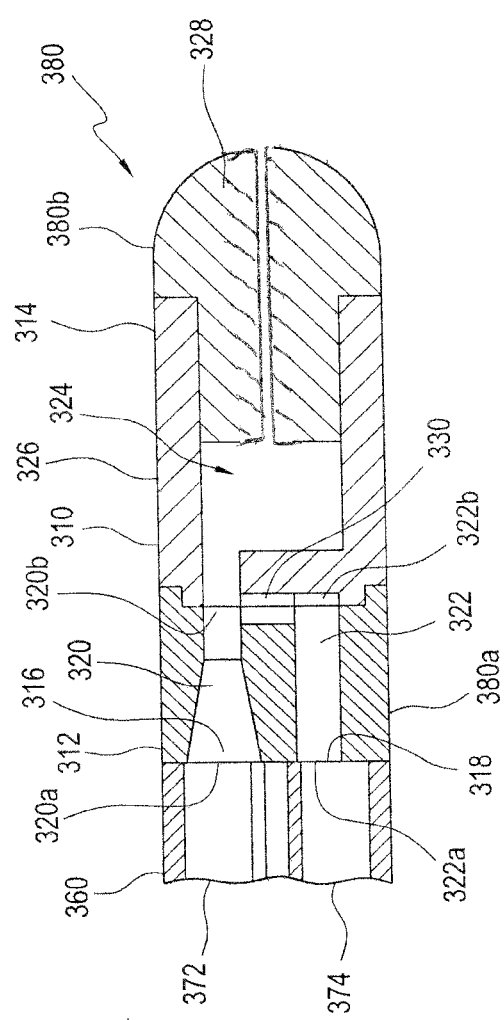
FIG. 6A
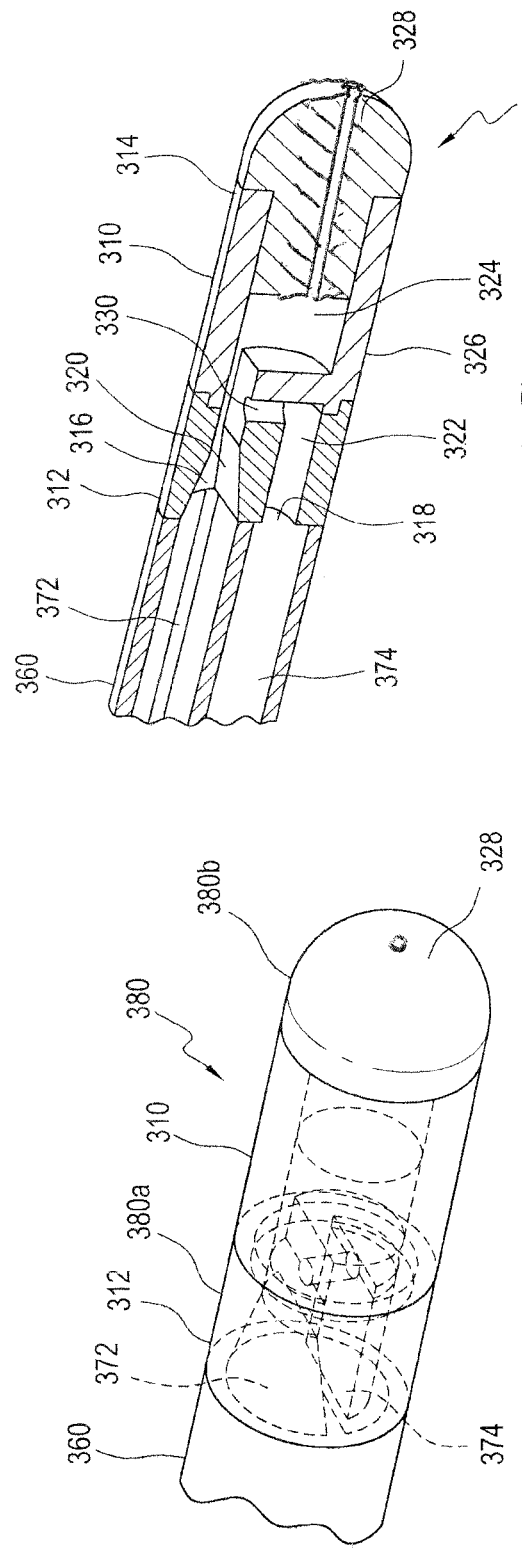
FIG. 6C
FIG. 6B

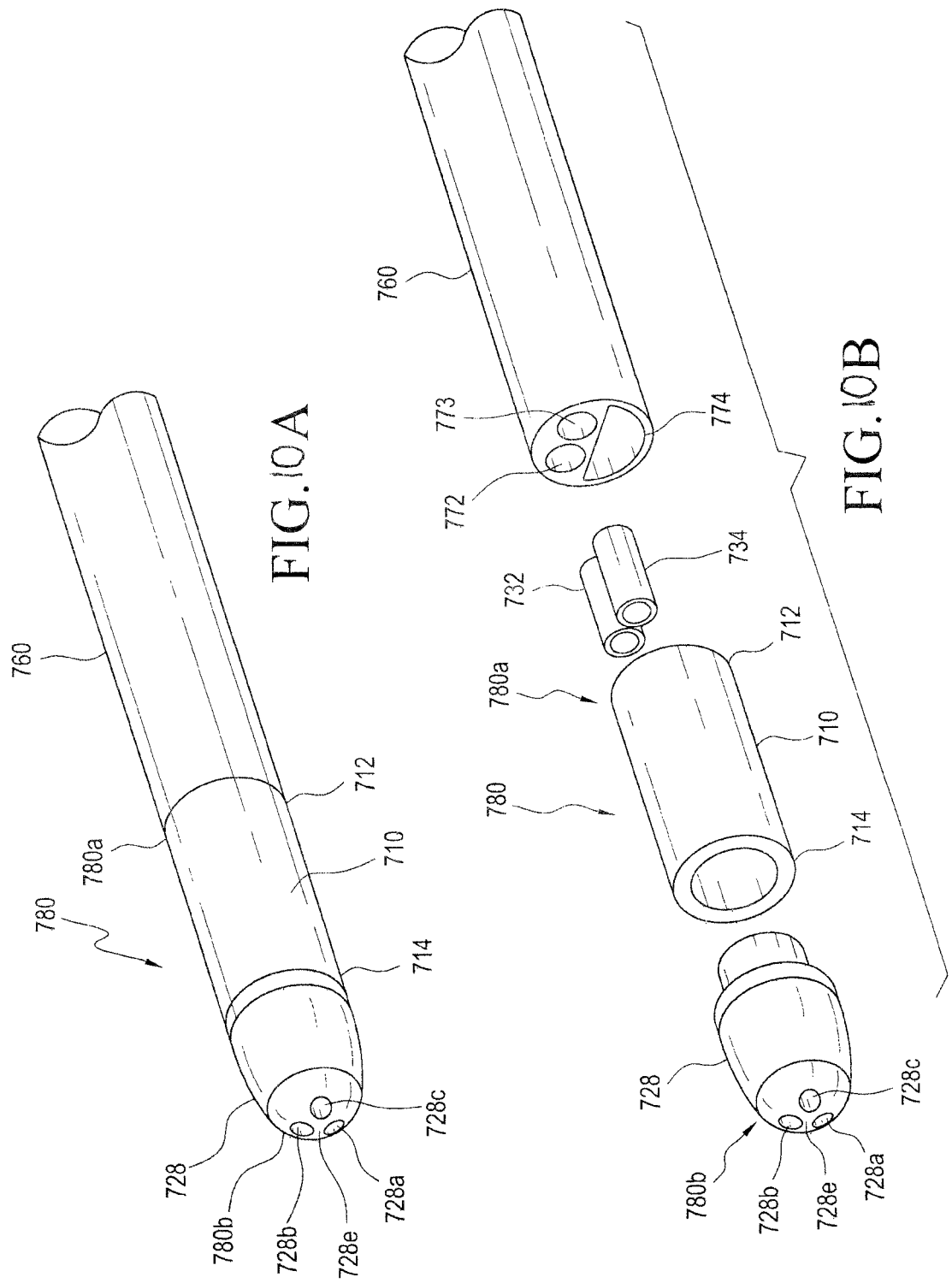

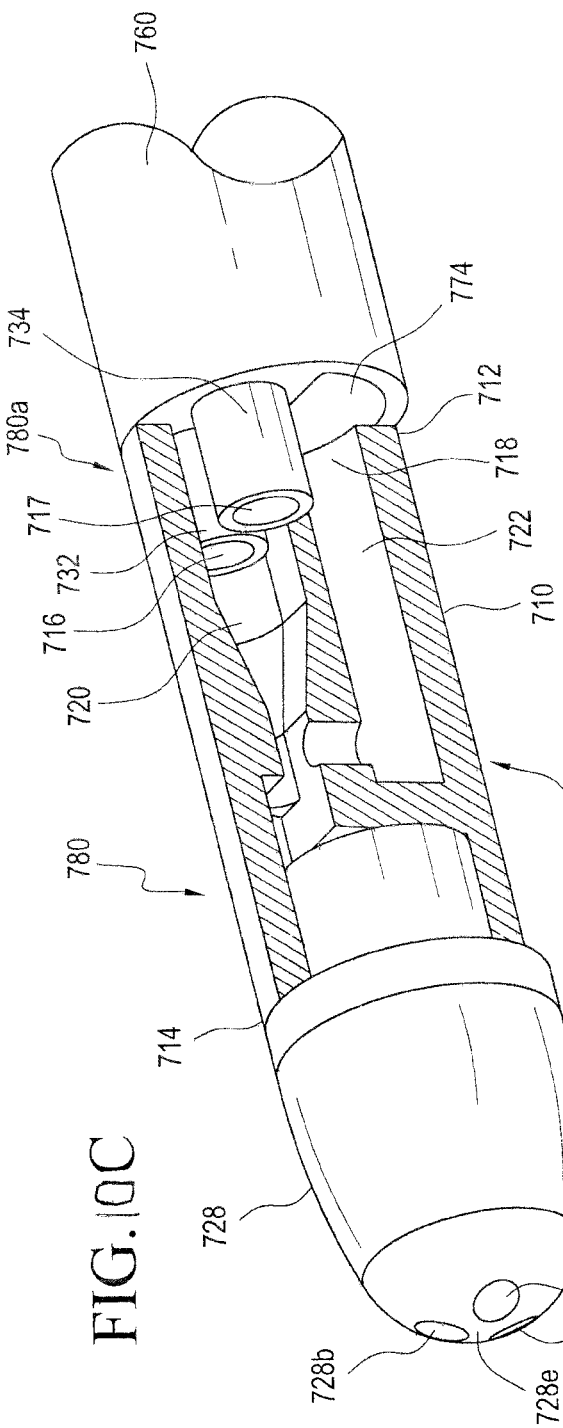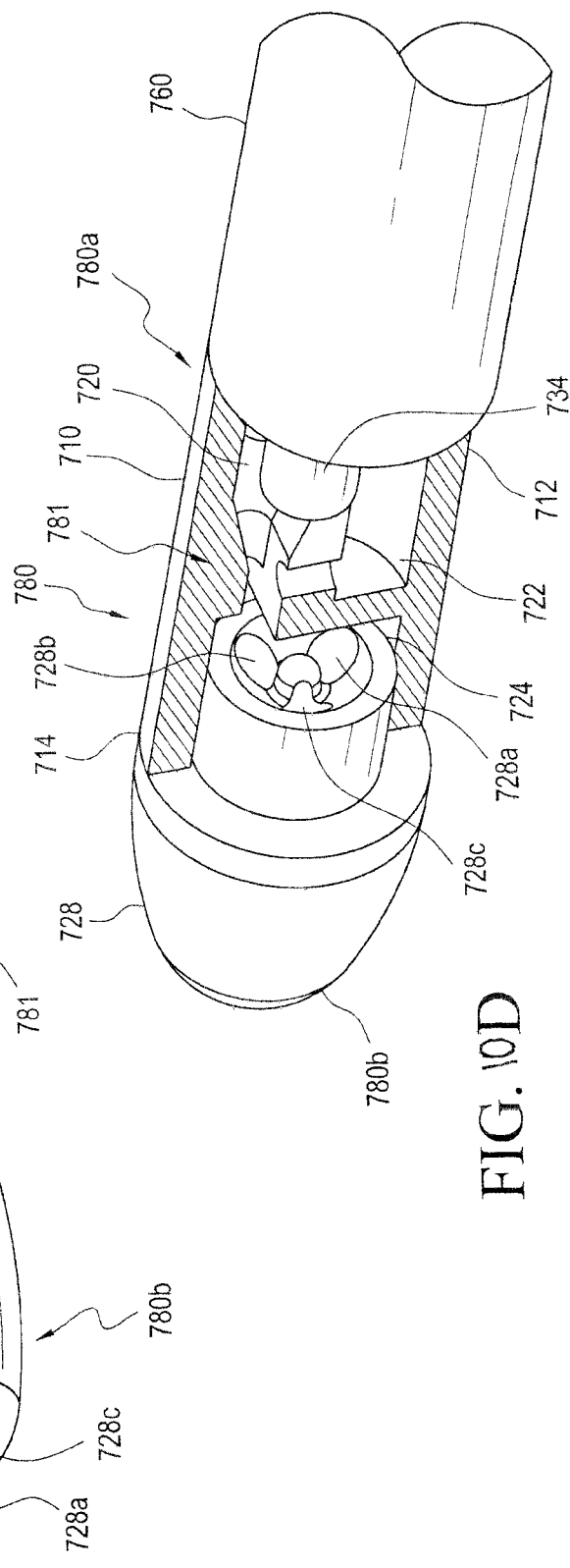

ial suspension of carbon dioxide ($CO_2$)

APPARATUS AND METHOD FOR PRODUCING AN ENRICHED MEDICAL SUSPENSION OF CARBON DIOXIDE

CROSS REFERENCE TO RELATED APPLICATION

This application is a continuation of U.S. patent application Ser. No. 16/424,616, entitled "APPARATUS AND METHOD FOR PRODUCING AN ENRICHED MEDICAL SUSPENSION OF CARBON DIOXIDE" filed May 29, 2019, which is currently pending, which is a continuation of U.S. patent application Ser. No. 15/696,772, entitled "APPARATUS AND METHOD FOR PRODUCING AN ENRICHED MEDICAL SUSPENSION OF CARBON DIOXIDE." filed Sep. 6, 2017, which is now U.S. Pat. No. 10,350,399, which is a continuation in part of U.S. patent application Ser. No. 15/053,530, entitled "APPARATUS AND METHOD FOR PRODUCING $CO_2$ ENRICHED MEDICAL FOAM," filed Feb. 25, 2016, which is now U.S. Pat. No. 10,155,093, which claims the benefit of U.S. Provisional Patent Application Ser. No. 62/121,827, entitled "CATHETER FOR PRODUCING $CO_2$ ENRICHED MEDICAL FOAM," filed Feb. 27, 2015, and this application is a continuation of U.S. patent application Ser. No. 16/424,616, entitled "APPARATUS AND METHOD FOR PRODUCING AN ENRICHED MEDICAL SUSPENSION OF CARBON DIOXIDE," filed May 29, 2019, which is currently pending, which is a continuation of U.S. patent application Ser. No. 15/696,772, entitled "APPARATUS AND METHOD FOR PRODUCING AN ENRICHED MEDICAL SUSPENSION OF CARBON DIOXIDE," filed Sep. 6, 2017, which is now U.S. Pat. No. 10,350,399, which is a continuation in part of U.S. patent application Ser. No. 15/053,530, filed Feb. 25, 2016, which is now U.S. Pat. No. 10,155,093, which is a continuation-in-part of U.S. patent application Ser. No. 14/509,459, entitled "APPARATUS AND PROCESS FOR PRODUCING $CO_2$ ENRICHED MEDICAL FOAM," filed Oct. 8, 2014, which is now U.S. Pat. No. 9,744,342, which is a continuation of U.S. patent application Ser. No. 13/068,680, entitled "APPARATUS AND PROCESS FOR PRODUCING $CO_2$ ENRICHED MEDICAL FOAM," filed May 17, 2011, which is now U.S. Pat. No. 8,876,749, which is a continuation-in-part of U.S. patent application Ser. No. 12/652,845, entitled "PORTABLE MEDICAL GAS DELIVERY SYSTEM," filed Jan. 6, 2010, which is abandoned, which is a continuation-in-part of U.S. patent application Ser. No. 12/210,368, entitled "PORTABLE MEDICAL FOAM APPARATUS," filed Sep. 15, 2008, which is abandoned, which is a continuation-in-part of U.S. patent application Ser. No. 11/945,674, entitled "PORTABLE EVAPORATIVE SNOW APPARATUS," filed Nov. 27, 2007, which is now U.S. Pat. No. 7,543,760, which claims the benefit of U.S. Provisional Patent Application Ser. No. 60/867,323, entitled "PORTABLE EVAPORATIVE SNOW APPARATUS," filed Nov. 27, 2006, the disclosures of which are incorporated herein by reference in their entirety.

BACKGROUND OF THE INVENTION

1. Field of the Invention

This invention relates to an apparatus and process for producing an enriched medical suspension of carbon dioxide ($CO_2$).

2. Description of the Related Art

The present invention utilizes the Venturi effect to produce an enriched medical suspension of carbon dioxide ($CO_2$) for use in various applications. The apparatus of the present invention is simple to manufacture and use because it does not require an impeller and incorporated fan in order to create and dispense the enriched medical suspension of carbon dioxide ($CO_2$).

The Venturi effect is an example of Bernoulli's principle, in the case of incompressible fluid flow through a tube or pipe with a constriction in it. The fluid velocity must increase through the constriction to satisfy the equation of continuity, while its pressure must decrease due to conservation of energy; the gain in kinetic energy is supplied by a drop in pressure or a pressure gradient force.

The limiting case of the Venturi effect is choked flow, in which a constriction in a pipe or channel limits the total flow rate through the channel because the pressure cannot drop below zero in the constriction. Choked flow is used to control the delivery rate of water and other fluids through spigots and other types of valves. The portable apparatus of the present invention utilizes a source of pressurized medical fluid, to produce the desired pressure and gas flow for the effective creation of an enriched medical suspension.

SUMMARY OF THE INVENTION

The present invention provides for a novel apparatus for producing an enriched medical suspension of carbon dioxide ($CO_2$) as well as a process for utilizing such enriched medical suspension in medical treatment, in particular, enhanced imaging via the application of carbon dioxide ($CO_2$). One embodiment of the present invention features an apparatus for producing and delivering an enriched medical suspension of carbon dioxide ($CO_2$) comprising (i) a suspension delivery catheter including a syringe containing carbon dioxide ($CO_2$), a dual lumen catheter and a Venturi-agitating tip assembly; and (ii) a compressed medical fluid unit having at least one container of pressurized medical carbon dioxide ($CO_2$) and the gas regulator valve.

The pressurized gas is preferably medical carbon dioxide ($CO_2$). However, it is appreciated other suitable pressurized gases may be used in accordance with the present invention.

The Venturi-agitating tip assembly includes a novel arrangement by which pressurized medical carbon dioxide ($CO_2$) enters a second end of the Venturi-agitating tip assembly through a gas inlet. The resultant pressure produced within the Venturi-agitating tip assembly draws a medical solution of carbon dioxide ($CO_2$) into the interior of the Venturi-agitating tip assembly through a second inlet. The pressurized medical carbon dioxide ($CO_2$) and the medical solution of carbon dioxide ($CO_2$) are mixed together to form an enriched medical suspension of carbon dioxide ($CO_2$) that continues to travel towards the first end of the Venturi-agitating tip assembly where the enriched medical suspension of carbon dioxide ($CO_2$) is sprayed upon the inner lumen of a vessel in order to provide an enriched medical suspension of carbon dioxide ($CO_2$) for the purpose of improved contrast. Thus, the enriched medical suspension of carbon dioxide ($CO_2$) can be delivered and applied by spraying or washing the enriched medical suspension of carbon dioxide ($CO_2$) upon the inner lumen of a vessel.

The present invention also relates to methods of medical treatments. In one embodiment the invention is a method for providing an enriched medical suspension of carbon dioxide ($CO_2$) applying such enriched medical suspension to the vascular system comprising the steps of: (i) providing a portable medical fluid apparatus; (ii) providing a container (for example, a syringe) with a medical solution of carbon dioxide ($CO_2$), the container having an entrance, an exit and a release means regulating the exit; (iii) attaching a medically acceptable directional device from the apparatus to the entrance of the container; (iv) initiating an actuator of the apparatus to release the pressurized medical carbon dioxide ($CO_2$); (v) activating the release mechanism to produce an enriched medical suspension of carbon dioxide ($CO_2$); and (vi) applying the enriched medical suspension of carbon dioxide ($CO_2$) to a predetermined vascular location via a catheter or needle.

In medical uses, $CO_2$ is used because it is safer and has fewer complications than air or oxygen in the same uses. $CO_2$ diffuses more naturally in body tissues and is absorbed in the body more rapidly and with fewer side effects. The present invention can deliver $CO_2$ from an adjustable port that controls the psi from 0 psi to 120 psi. Previous methods utilizing large $CO_2$ tanks and regulators are dangerous because of the risk of a seal, valve, or part malfunction causing a projectile in a medical setting and the potential for explosive delivery. The present invention is safer as it eliminates these possibilities of malfunction.

The present invention requires very little space to store, as opposed to the cumbersome existing tank systems and is much easier to use, with a push button actuator to initiate operation. The present invention is much less expensive than current $CO_2$ tank systems. Acquisition of the $CO_2$ in the present invention now requires only cartridges which can be delivered in a small box. The current tanks require filling at a filling station which involves the transport of a large quantity of $CO_2$ which is ultimately inconvenient.

BRIEF DESCRIPTION OF THE DRAWINGS

Other objects, features and advantages will occur from the following description of a preferred embodiment and the accompanying drawings.

FIGS. 6A, 6B and 6C respectively show a longitudinal cross sectional view, a perspective view and a perspective cross sectional view of a Venturi-agitating tip assembly in accordance with an alternate first embodiment.

FIGS. 10A, 10B, 10C, 10D and 10E are respectively a perspective view, an exploded view, a front partial cross-sectional view, a rear partial cross-sectional view and a lateral cross-sectional view in accordance with a fifth embodiment;

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

With reference to the various figures and embodiments, a medical fluid suspension generating apparatus for performing medical procedures includes a Venturi-agitating tip assembly composed of a multi-channel arrangement at a proximal first end thereof and a tip at a distal second end thereof. The apparatus also includes a compressed medical fluid unit including pressurized medical carbon dioxide ($CO_2$) fluidly connected to the multi-channel arrangement at a proximal first end of the Venturi-agitating tip assembly and a medical solution of carbon dioxide ($CO_2$) fluidly connected to the multi-channel arrangement at a proximal first end of the Venturi-agitating tip assembly. Pressurized gas, from the compressed medical fluid unit, and the medical solution of carbon dioxide are combined within the Venturi-agitating tip assembly in a manner generating an enriched medical suspension that is ultimately dispensed from the suspension delivery apparatus. Through the use of the present medical fluid suspension generating apparatus procedures may be performed without the use of tumescent anesthesia, thereby alleviating discomforting for patients and simplifying procedures to medical practitioners.

Figure 1:
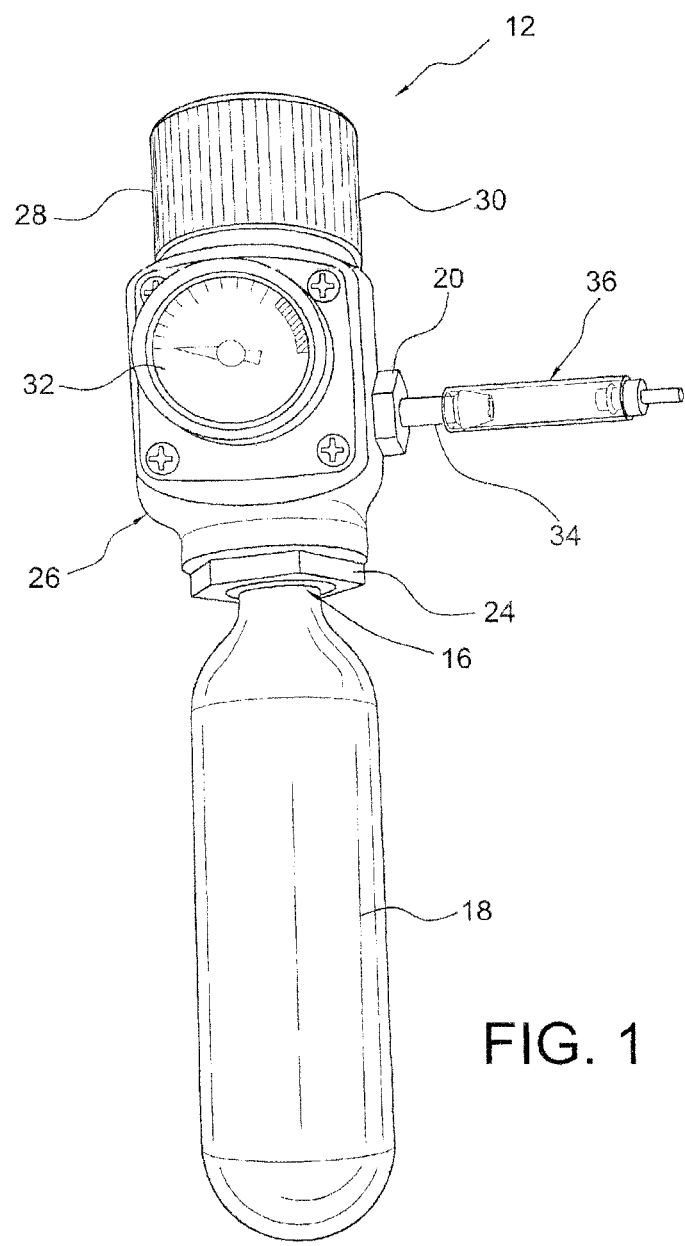
FIG. 1 is a perspective view of the compressed medical fluid unit with a capsule secured thereto.
Figure 2:
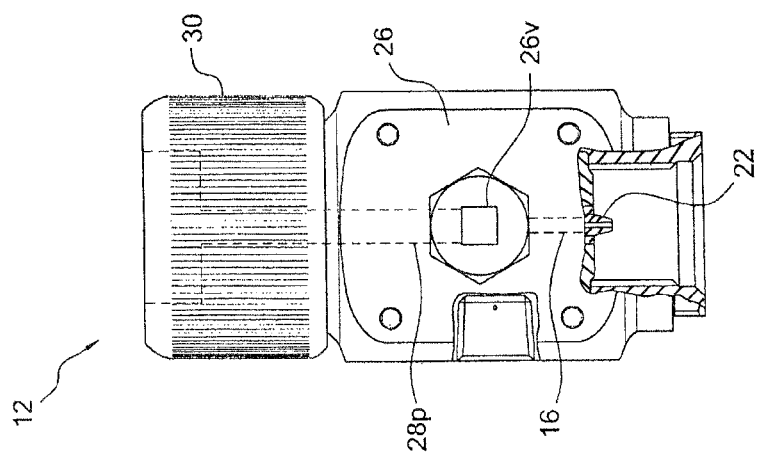
FIG. 2 is a front elevation view of the compressed medical fluid unit with a capsule secured thereto.
Figure 3:
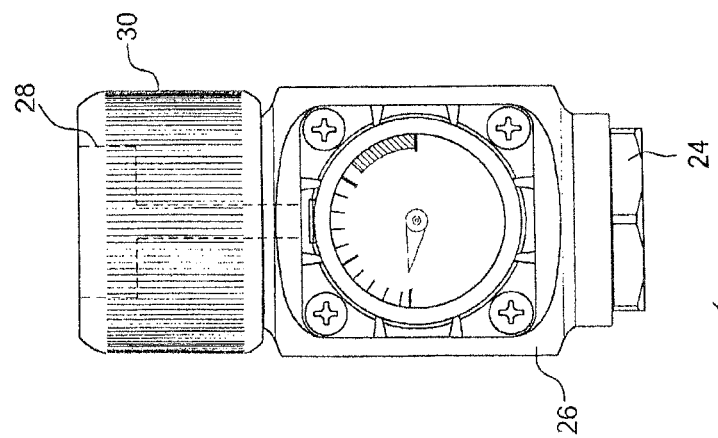
FIG. 3 is a side elevation view of the compressed medical fluid unit shown in FIG. 2 with a partial cutaway of the fitting to show the cylinder cartridge puncture valve.

With reference to FIGS. 1, 2 and 3, the compressed medical fluid unit 12 is disclosed. The compressed medical fluid unit 12 is disclosed in detail in U.S. patent application Ser. No. 14/957,657, filed Sep. 26, 2014, entitled "DELIVERY SYSTEM FOR THE EFFECTIVE, RELIABLE AND FOOLPROOF DELIVERY OF CONTROLLED AMOUNTS OF A MEDICAL FLUID," which is incorporated herein by reference. With reference to FIGS. 1, 2 and 3, the compressed medical fluid unit 12 includes an inlet port 16 to which a source of pressurized medical fluid, for example, a pressurized gas cylinder containing medical carbon dioxide ($CO_2$) 18 is selectively connected and an outlet port 20 in communication with the inlet port 16, and ultimately the at least one pressurized gas ($CO_2$) cylinder 18.

The pressurized gas cylinder 18 is secured to, and maintained in fluid communication with, the integrated compressed medical fluid unit 12 by a cylinder cartridge puncture valve 22 and a fitting 24 formed at the inlet port 16 of the compressed medical fluid unit 12. In accordance with a preferred embodiment, the cylinder cartridge puncture valve 22 has a mechanism for piercing the pressurized gas cylinder 18, as is known in the art, and for holding or securing the pressurized gas cylinder 18 in place.

The pressurized gas exits the inlet port 16 and passes through a regulator valve assembly 26 controlled by a press button actuator 28 and regulator adjustment dial 30. The regulator valve assembly 26 dictates the pressure of the gas as it ultimately exits the outlet port 20. In accordance with a preferred embodiment, the regulator valve assembly 26 has a selective outlet pressure in the range of 7 psi to 19 psi. The outlet pressure is achieved by rotating the regulator adjustment dial 30 of the button actuator 28. In addition, to regulating the applied pressure, the regulator valve assembly 26 also includes a valve 26v that controls the passage of gas from the inlet port 16 to the outlet port 20. The valve 26v is controlled via a push button mechanism 28p in the button actuator 28 such that a user may selectively determine when gas may pass therethrough to the outlet port 20. In accordance with a preferred embodiment, the $CO_2$ flow rate is less than 12 NL/min (normal liters per minute).

As mentioned above, the regulator valve assembly 26 also includes a regulator adjustment dial 30 which controls the pressure permitted to exit the outlet port 20 by either rotating the regulator adjustment dial 30 clockwise or counterclockwise as may be desired to adjust the applied pressure. The applied pressure may be monitored using the PSI gauge formed on the front face 32 of the integrated compressed medical fluid unit 12.

In practice, a pressurized gas cylinder 18 is applied to the compressed medical fluid unit 12 in the following manner. The adjustment dial 30 is first disengaged (loosened) by rotating the same in a counter-clockwise direction so as to prevent the passage of pressurized gas therethrough. The pressurized gas cylinder 18 is then screwed into the fitting 24 and the cylinder cartridge puncture valve 22 punctures pressurized gas cylinder 18. The system is then actuated as by twisting the adjustment dial in a clockwise direction until a desired pressure is established and operating the same as described above through the manipulation of the press button actuator 28 and the adjustment dial 30.

As mentioned above, the outlet port 20 is in fluid communication with the inlet port 16 for transport of pressurized medical carbon dioxide ($CO_2$) in accordance with the present invention. The outlet port 20 is provided with a luer connection 34 for the secure and selective attachment of an outlet tube 36 thereto.

As briefly mentioned above, the pressurized gas cylinder 18 is secured to the compressed medical fluid unit 12 by a cartridge puncture valve 22 as is commonly known. Pressurized medical carbon dioxide ($CO_2$) leaves the regulator valve assembly 26 at the regulator adjusted pressure and goes to the outlet port 20.

In accordance with an alternate embodiment, an integrated compressed medical fluid unit as disclosed in U.S. patent application Ser. No. 14/497,691, filed Sep. 26, 2014, entitled "SYSTEM AND METHOD FOR THE EFFECTIVE, RELIABLE AND FOOLPROOF DELIVERY OF CONTROLLED AMOUNTS OF A MEDICAL FLUID," which is incorporated herein by reference, may be utilized in accordance with the present invention.

Figure 4:
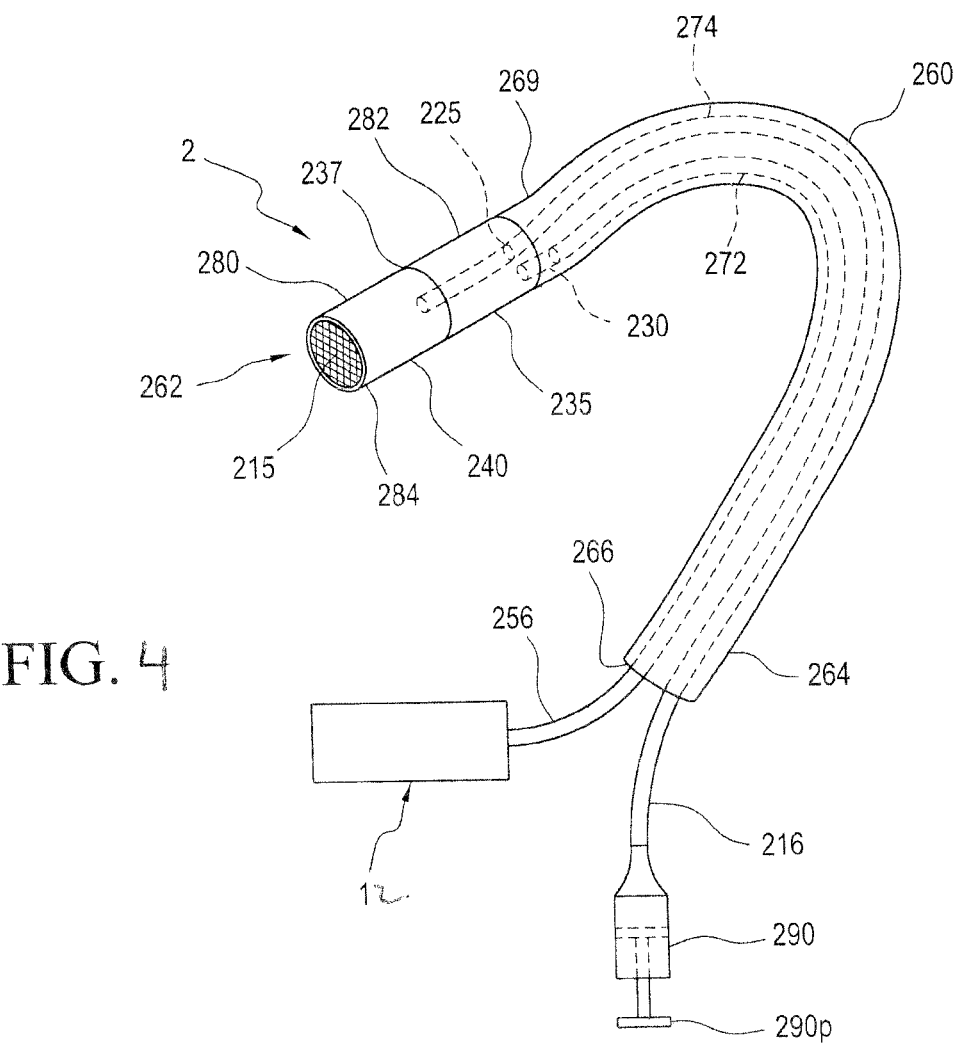
FIG. 4 is a perspective view of the suspension delivery catheter and a syringe containing a medical solution of carbon dioxide ($CO_2$).

With reference to FIG. 4, a suspension delivery catheter 2 features a dual lumen catheter 260 connecting a Venturi-agitating tip assembly 280 to pressurized medical carbon dioxide ($CO_2$) from the compressed medical fluid unit 12 and a medical solution of carbon dioxide ($CO_2$) from a syringe 290. The syringe 290 includes a one-way valve at its outlet to ensure that medical solution of carbon dioxide ($CO_2$) from the syringe 290 only flows out of the syringe 290. The suspension delivery catheter 2 includes a first end (or distal end) 262 having the Venturi-agitating tip assembly 280 and a second end (or proximal end) 264 to which the compressed medical fluid unit 12 and the medical solution of carbon dioxide ($CO_2$) are fluidly connected for the passage of pressurized medical carbon dioxide ($CO_2$) and medical solution of carbon dioxide ($CO_2$). As will be appreciated based upon the following disclosure, a dual lumen catheter 260 is connected to the Venturi-agitating tip assembly by securing a medical fluid hose inlet 230 and a suspension delivery line 225 of the Venturi-agitating tip assembly 280 to a first lumen 272 and a second lumen 274 of the dual lumen catheter 260, respectively. The provision of the Venturi-agitating tip assembly 280 at the very end of the catheter allows for the mixing of pressurized medical carbon dioxide ($CO_2$) and the medical solution of carbon dioxide ($CO_2$) immediately adjacent the discharge point.

A micro hose 256 connects the compressed medical fluid unit 12 to the first lumen 272 of the dual lumen catheter 260 at a proximal first end 266 thereof for the transmission of the pressurized medical carbon dioxide ($CO_2$) from compressed medical fluid unit 12 to the Venturi-agitating tip assembly 280. As such, pressurized medical carbon dioxide ($CO_2$) leaving the compressed medical fluid unit 12 via the outlet air port 25 enters the first lumen 272 of the dual lumen catheter 260 via micro hose 256. After passing through the first lumen 272 of the dual lumen catheter 260, the pressurized medical carbon dioxide ($CO_2$) passes through medical fluid hose inlet 230 of the Venturi-agitating tip assembly 280 and enters the Venturi-agitating tip assembly 280 of the suspension delivery catheter 2. As will be explained below in greater detail, the medical fluid suspension of carbon dioxide ($CO_2$) generated at the Venturi-agitating tip assembly 280 is directly applied to a vein requiring treatment with the medical fluid of carbon dioxide ($CO_2$).

As to the connection of the medical solution of carbon dioxide ($CO_2$) to the suspension delivery catheter 2, the medical solution of carbon dioxide ($CO_2$) is delivered to the second lumen 274 of the dual lumen catheter 260 at the proximal first end 266 thereof, and ultimately to the Venturi-agitating tip assembly 280, via a container, in particular, a syringe 290, connected to the second lumen 274 of the dual lumen catheter 260 by a supply line 216. As discussed above, the syringe 290 includes a one-way valve at its outlet to ensure that medical solution of carbon dioxide ($CO_2$) from the syringe 290 only flows out of the syringe 290. After passing through the second lumen 274 of the dual lumen catheter 260, the medical solution of carbon dioxide ($CO_2$) from the syringe 290 travels into the solution delivery line 225 of the Venturi-agitating tip assembly 280 where it is combined with pressurized medical carbon dioxide ($CO_2$) from the compressed medical fluid unit 12 to form an enriched medical suspension of carbon dioxide ($CO_2$).

Figure 5:
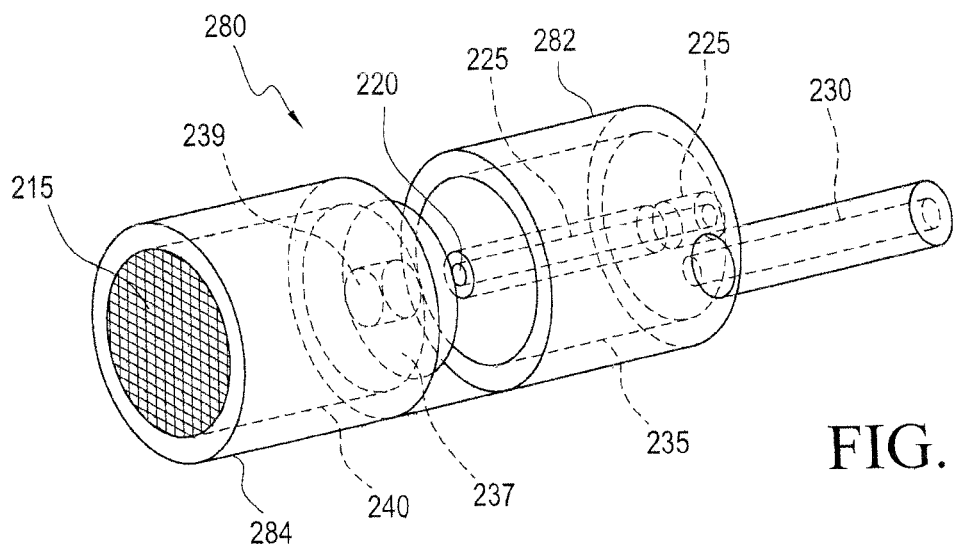
FIG. 5 is a close-up exploded view of the Venturi-agitating tip assembly shown in FIG. 4.

As shown in FIGS. 4 and 5, and as briefly discussed above, the Venturi-agitating tip assembly 280 includes a proximal first end 282 and a distal second end 284. The Venturi-agitating tip assembly 280 includes an upper chamber 240 at the distal second end 284 of the Venturi-agitating tip assembly 280 and a lower chamber 235 at the proximal first end 282 of the Venturi-agitating tip assembly 280, wherein a distal second end 269 of the dual lumen catheter 260 is fluidly coupled to the lower chamber 235 at the proximal first end 282 of the Venturi-agitating tip assembly 280. The upper chamber 240 and the lower chamber 235 are separated by a wall 237 having an aperture 239 formed therein allowing for the passage of pressurized medical carbon dioxide ($CO_2$) released in the lower chamber 235 to pass into the upper chamber 240.

The suspension delivery line 225 passes through the lower chamber 235 and has an outlet 220 for delivering medical solution of carbon dioxide ($CO_2$) into the upper chamber 240. The medical solution of carbon dioxide ($CO_2$) is delivered to the suspension delivery line 225 via the syringe 290 and the dual lumen catheter 260. More particularly, the medical solution of carbon dioxide ($CO_2$) from the syringe 290 travels through the second lumen 274 of the dual lumen catheter 260 and into the solution delivery line 225 when pressurized medical carbon dioxide ($CO_2$) enters the Venturi-agitating tip assembly 280 through the inlet 230 after being actuated and released from the compressed medical fluid unit 12. The pressurized medical carbon dioxide ($CO_2$) entering the Venturi-agitating tip assembly 280 imparts negative pressure on the medical solution of carbon dioxide ($CO_2$) in the syringe 290 and draws the medical solution of carbon dioxide ($CO_2$) from the syringe 290 through the supply line 216, through the second lumen 274 of the dual lumen catheter 260, and into the solution delivery line 225 due to the Venturi effect. The syringe plunger 290$p$ is used to regulate or stop flow of medical solution of carbon dioxide ($CO_2$) from the syringe 290. Pressurized medical carbon dioxide ($CO_2$) traveling from the lower chamber 235 of the Venturi-agitating tip assembly 280 to the upper chamber 240 of the Venturi-agitating tip assembly via aperture 239 in the wall 237 creates negative pressure inside the Venturi-agitating tip assembly 280, such that the medical solution of carbon dioxide ($CO_2$) exiting the outlet 220 of the solution delivery line 225 mixes with pressurized medical carbon dioxide ($CO_2$) in the solution delivery line 225 and ultimately forms an enriched medical suspension of carbon dioxide ($CO_2$) that is sprayed upon the inner lumen of a vessel via the spray tip 215. The force of the pressurized medical carbon dioxide ($CO_2$) traveling through the Venturi-agitating tip assembly 280 and exiting through the spray tip as part of an enriched medical suspension of carbon dioxide ($CO_2$) projects the enriched medical suspension of carbon dioxide ($CO_2$) from the distal second end 284 of the Venturi-agitating tip assembly 280 as a spray and onto the inner lumen of a vessel.

It is appreciated various tip assemblies and enriched medical suspension generating structures may be employed in accordance with the present invention. In accordance with a first alternate embodiment as shown with reference to FIGS. 6A-6C, the Venturi-agitating tip assembly 380 employs a Venturi arrangement with a mixing chamber 324. The Venturi-agitating tip assembly 380 has a proximal first end 380$a$ and a distal second end 380$b$. The Venturi-agitating tip assembly 380 includes a hollow cylindrical elongated body 310 having a proximal first end 312, which coincides with the proximal first end 380$a$ of the Venturi-agitating tip assembly 380, and a distal second end 314. The proximal first end 380$a$ of the Venturi-agitating tip assembly 380 includes a multi-channel arrangement 381 including first and second inputs 316, 318 for attachment to the dual lumen catheter 360. The first and second inputs 316, 318 respectively lead to a first channel 320 and a second channel 322 of the multi-channel arrangement 381 of the Venturi-agitating tip assembly 380. The first and second channels 320, 322 lead to, and are in fluid communication with, a mixing chamber 324 (which also forms part of the multi-channel arrangement 381) located in the central portion 326 of the Venturi-agitating tip assembly 380, that is, between the proximal first end 380$a$ and the distal second end 380$b$. Located at the distal second end 380$b$ of the Venturi-agitating tip assembly 380, and secured to the distal second end 314 of the elongated body 310, is a spray tip 328 directing the enriched medical suspension of carbon dioxide ($CO_2$) in a spray pattern onto the inner lumen of a vessel.

The first channel 320 and the second channel 322 are interconnected in a manner creating a Venturi effect causing the pressurized medical carbon dioxide ($CO_2$) to effectively pull the medical solution of carbon dioxide ($CO_2$) through the second channel 322 and into the mixing chamber 324. This is achieved by providing with the first channel 320 with a reduced diameter as it extends from the proximal first end 312 of the elongated body 310 (that is, the first end 320$a$ of the first channel 320) to the central portion 326 of the Venturi-agitating tip assembly 380 (that is, the second end 320$b$ of the first channel 320). In accordance with a preferred embodiment, the diameter of the first channel 320 decreases from a diameter of 0.038 inches adjacent the proximal first end 312 of the elongated body 310 to a diameter of 0.017 inches adjacent the mixing chamber 324.

As mentioned above, the second channel 322 is in fluid communication with the first channel 320. This is achieved by the provisional of a transverse channel 330 connecting the second end 320$b$ of the first channel 320 with the second end 322$b$ of the second channel 322. In particular, the second channel 322 includes a first end 322$a$ adjacent the proximal first end 312 of the elongated body 310 and a second end 322$b$ adjacent the mixing chamber 324 (although not directly in fluid communication with the mixing chamber 324) and the transverse channel 330. In accordance with a preferred embodiment, the diameter of the second channel 322 is 0.031 inches and remains consistent as it extends from the first end 322$a$ thereof to the second end 322$b$ thereof.

The first lumen 372 of a dual lumen catheter 360 supplies the pressurized medical carbon dioxide ($CO_2$) and the second lumen 374 supplies the medical solution of carbon dioxide ($CO_2$). As such, the first lumen 372 is connected to, and in fluid communication with, the first channel 320 of the Venturi-agitating tip assembly 380 and the second lumen 374 is connected to, and in fluid communication with, the second channel 322 of the Venturi-agitating tip assembly 380. In practice, and as described above in conjunction with the prior embodiment, the medical solution of carbon dioxide ($CO_2$) from the syringe 290 travels through the second lumen 374 of the dual lumen catheter 360 and into the second channel 322 when pressurized medical carbon dioxide ($CO_2$) gas enters the first channel 320 and passes the transverse channel 330 into the mixing chamber 324 after being actuated and released from the compressed medical fluid unit 12. The pressurized medical carbon dioxide ($CO_2$) entering the Venturi-agitating tip assembly 380 imparts negative pressure on the medical solution of carbon dioxide ($CO_2$) in the syringe 290 and draws the medical solution of carbon dioxide ($CO_2$) from the syringe 290 through the second channel 322, through the second lumen 374 of the dual lumen catheter 360, and into the mixing chamber 324 due to the Venturi effect. The medical solution of carbon dioxide ($CO_2$) and the pressurized medical carbon dioxide ($CO_2$) are then mixed within the mixing chamber 324 to form an enriched medical suspension of carbon dioxide ($CO_2$). The syringe plunger 290$p$ is used to regulate or stop flow of medical solution of carbon dioxide ($CO_2$) from the syringe 290.

The pressurized medical carbon dioxide ($CO_2$) and medical solution of carbon dioxide ($CO_2$) mixing in the mixing chamber 324 are then forced through the spray tip 328 from which the enriched medical suspension of carbon dioxide ($CO_2$) is sprayed upon the inner lumen of a vessel. The force of the pressurized medical carbon dioxide ($CO_2$) traveling through the Venturi-agitating tip assembly 380 and exiting through the spray tip as part of an enriched medical suspension of carbon dioxide ($CO_2$) projects the enriched medical suspension of carbon dioxide ($CO_2$) from the distal second end 384 of the Venturi-agitating tip assembly 380 as a spray and onto the inner lumen of a vessel.

In accordance with a second embodiment as shown with reference to FIGS. 7A-7D, a Venturi-agitating tip assembly 480 employs a sintered material tip 428 in conjunction with a multi-channel arrangement 481 where the pressurized medical carbon dioxide ($CO_2$) and medical solution of carbon dioxide ($CO_2$) are mixed and forced through the spray tip 428. The Venturi-agitating tip assembly 480 includes a proximal first end 480a and a distal second end 480b. The Venturi-agitating tip assembly 480 includes a hollow cylindrical elongated body 410 having a proximal first end 412, which coincides with the proximal first end 480a of the Venturi-agitating tip assembly 480, and a distal second end 414. The Venturi-agitating tip assembly 480 is adapted for use with a dual lumen catheter 460, in particular a dual lumen catheter having concentric lumens, wherein the outer first lumen 472 is annular shaped for the passage of pressurized medical carbon dioxide ($CO_2$) (and has an outer diameter of 0.092 inches at the outer wall thereof and an inner diameter of 0.042 inches at the inner wall thereof) and the inner second lumen 474 is circular shaped for the passage of the medical solution of carbon dioxide ($CO_2$) (and has a diameter of 0.030 inches). The inner second lumen 474 is supported within the outer first lumen 472 by first and second radially extending rib members 473a, 473b (each having a thickness of 0.006 inches) that extend from the outer surface of the second lumen 474 to the inner surface of the outer first lumen 472. In this way the outer first lumen 472 is divided into first and second semicircular passageways 475a, 475b.

The proximal first end 480a of the Venturi-agitating tip assembly 480, in particular, the proximal first end 412 of the elongated body 410 is formed with two projections 432, 434 shaped and dimensioned for engagement within the outer first lumen 472 of the catheter 460 in a manner blocking a substantial portion of the outer first lumen 472. The two projections 432, 434 are arcuate members shaped and dimensioned to respectively block substantial portions of the first and second semicircular passageways 475a, 475b while creating four small passageways 436, each of approximately 0.031 inches (along the Y-axis as shown in FIG. 5D) by 0.050 inches (along the X-axis as shown in FIG. 5D) for the passage of pressurized medical carbon dioxide ($CO_2$) therethrough. The four small passageways 436 are defined by spaces existing between the edges of the arcuate members 432, 434 and the first and second radially extending rib members 473a, 473b.

The remainder of the Venturi-agitating tip assembly 480 includes a central mixing chamber 424 that is in fluid communication with the second lumen 474 and the four small passageways 436 feeding pressurized medical carbon dioxide ($CO_2$) from the first lumen 472. Secured to, and closing off, the second end 414 of the elongated body 410 is a spray tip 428, which is thereby positioned at the distal second end 480b of the Venturi-agitating tip assembly 480. Attachment of the spray tip 428 to the elongated body 410 is achieved by providing the spray tip 428 with a projection 438 that seats within the opening at the second end 414 of the elongated body 410.

The first lumen 472 and the second lumen 474 are interconnected in a manner causing the pressurized medical carbon dioxide ($CO_2$) to effectively pull the medical solution of carbon dioxide ($CO_2$) through the second lumen 474 and into the mixing chamber 424. In practice, the medical solution of carbon dioxide ($CO_2$) from the syringe 290 travels through the second lumen 474 of the dual lumen catheter 460 and into the mixing chamber 424 when pressurized medical carbon dioxide ($CO_2$) passes through the four small passageways 436 and enters the mixing chamber 424 (where the medical solution of carbon dioxide ($CO_2$) from the syringe 290 and the pressurized medical carbon dioxide ($CO_2$) mix to form an enriched medical suspension of carbon dioxide ($CO_2$)) after being actuated and released from compressed medical fluid unit 12. The pressurized medical carbon dioxide ($CO_2$) entering the mixing chamber 424 imparts negative pressure on the medical solution of carbon dioxide ($CO_2$) in syringe 290 and draws the medical solution of carbon dioxide ($CO_2$) from the syringe 290 through the second lumen 474 and into the mixing chamber 424. The syringe plunger 290p is used to regulate or stop flow of medical solution of carbon dioxide ($CO_2$) from the syringe 290.

The pressurized medical carbon dioxide ($CO_2$) and medical solution of carbon dioxide ($CO_2$) mixing in the mixing chamber 424 are then forced through the spray tip 428 from which an enriched medical suspension of carbon dioxide ($CO_2$) is sprayed upon the inner surface of a lumen. The force of the pressurized medical carbon dioxide ($CO_2$) traveling through the Venturi-agitating tip assembly 480 and exiting through the spray tip as part of an enriched medical suspension of carbon dioxide ($CO_2$) projects the enriched medical suspension of carbon dioxide ($CO_2$) from the distal second end 484 of the Venturi-agitating tip assembly 480 as a spray and onto the inner lumen of a vessel.

Figure 7D:
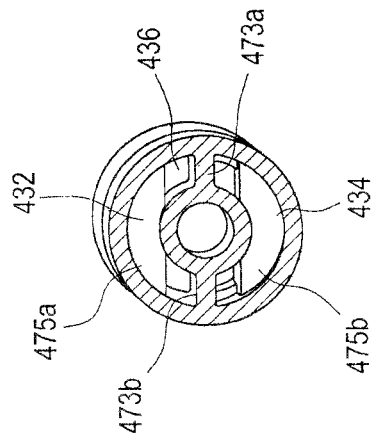
FIGS. 7A, 7B, 7C and 7D are respectively a perspective view, a longitudinal cross-sectional perspective view, an exploded view and a lateral cross-sectional view of a Venturi-agitating tip assembly in accordance with an alternate second embodiment.
Figure 7C:
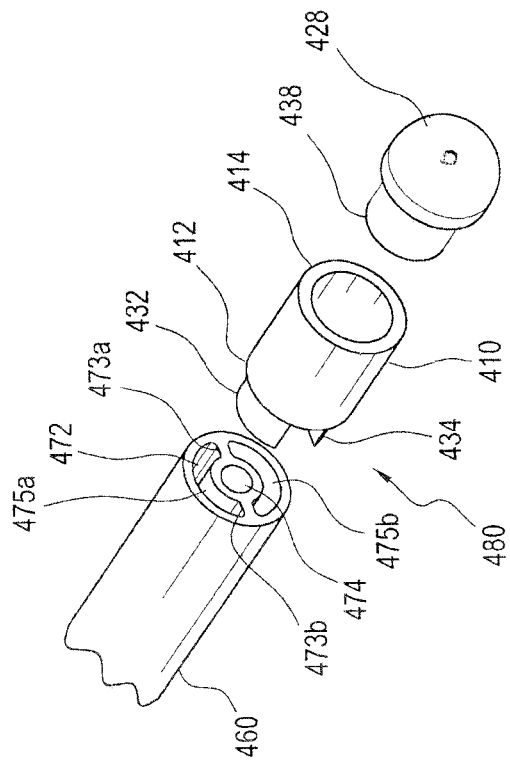
Figure 7A:
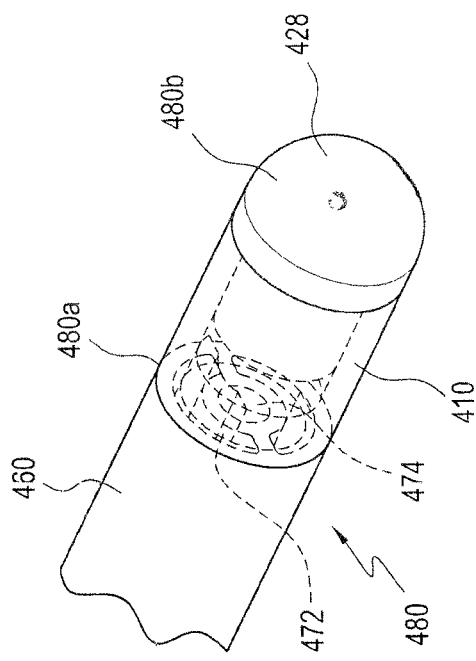
Figure 7B:
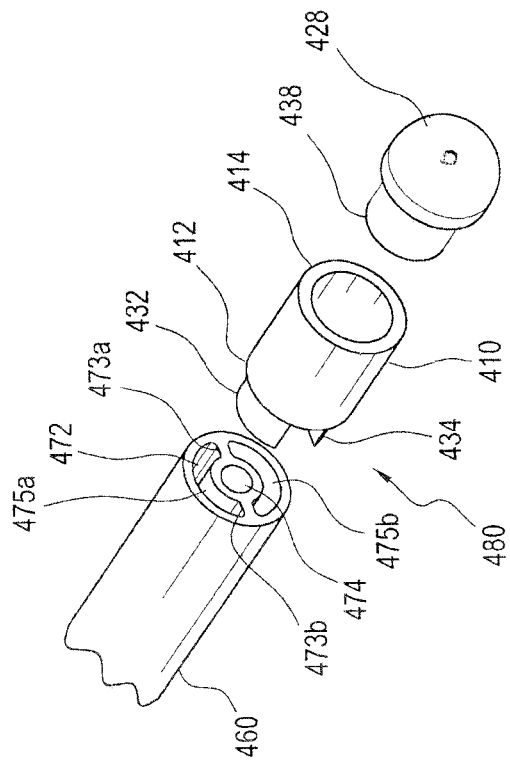
Figure 8:
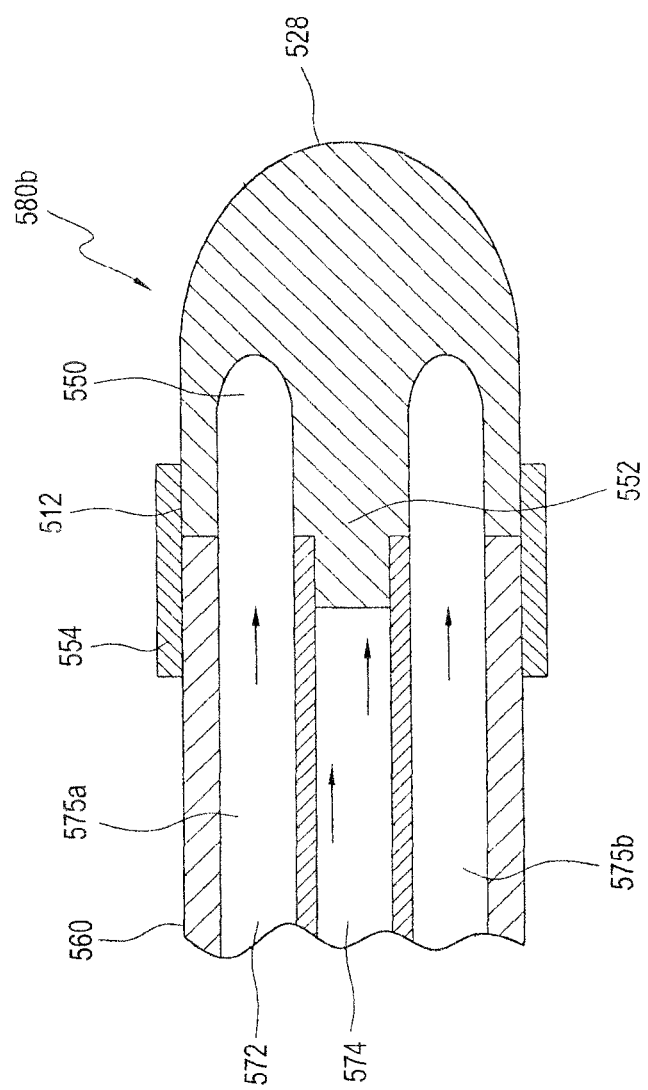
FIG. 8 is a cross-sectional view of a Venturi-agitating tip assembly in accordance with an alternate third embodiment.
Figure 9B:
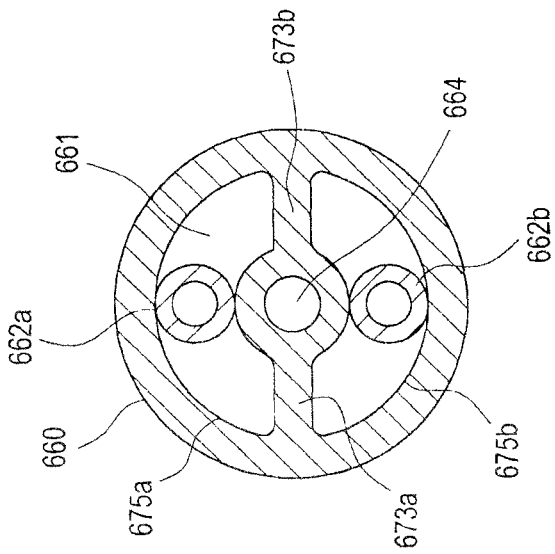
FIGS. 9A and 9B are respectively a longitudinal cross-sectional view and a lateral cross-sectional view of a Venturi-agitating tip assembly in accordance with an alternate fourth embodiment.
Figure 9A:
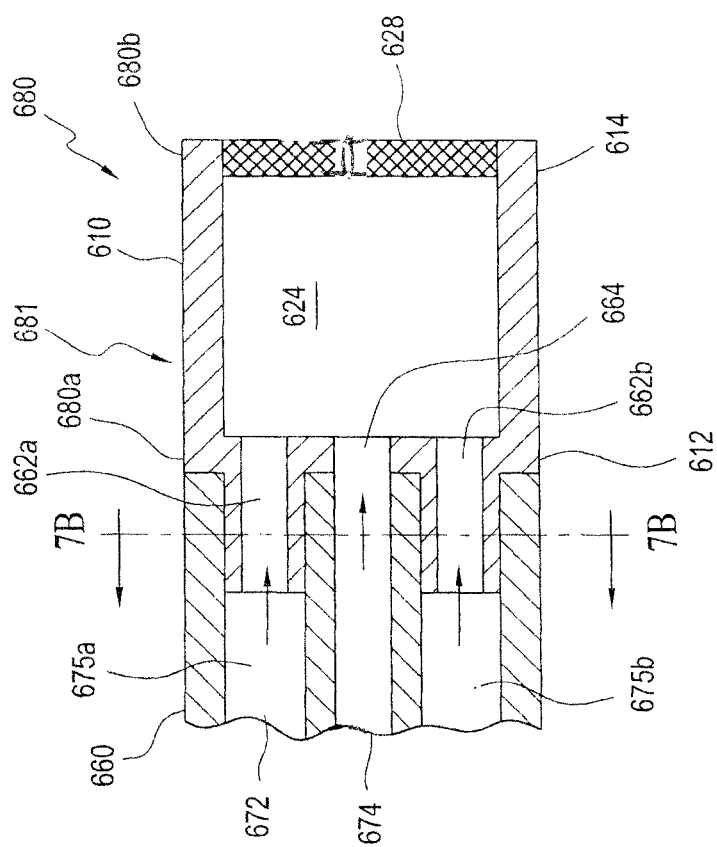
Figure 10E:
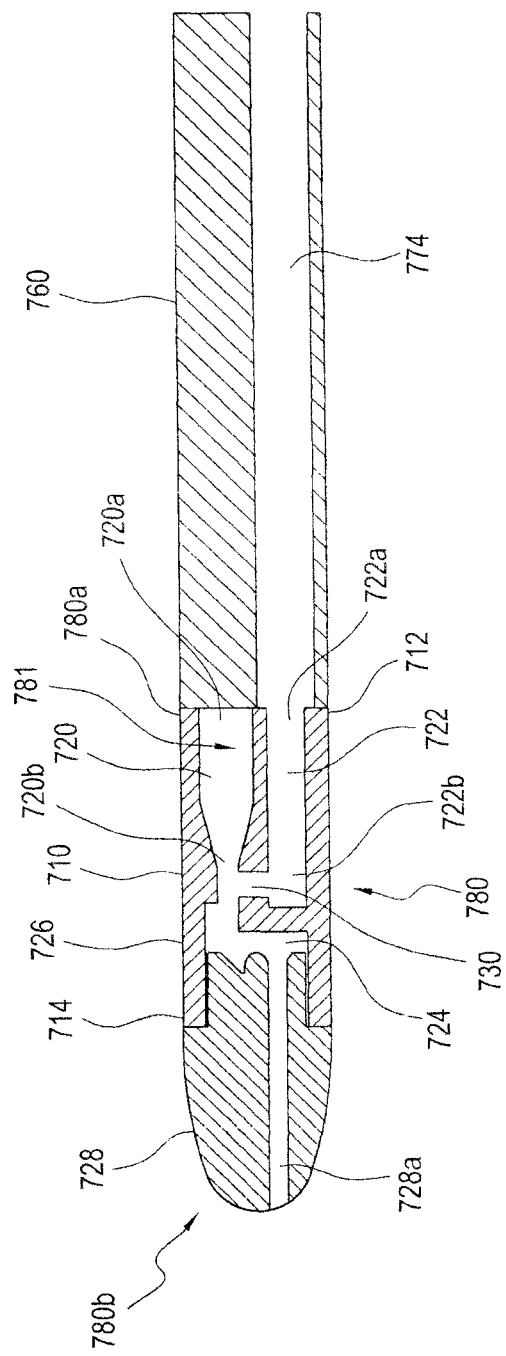

In accordance with a third embodiment as shown with reference to FIG. 8, a Venturi-agitating tip assembly 580 is composed solely of a porous sintered material tip 528 shaped and dimensioned for attachment to the end of a dual lumen catheter 560, in particular, a dual lumen catheter 560 having concentric lumens, wherein the outer first lumen 572 is annular shaped for the passage of pressurized medical carbon dioxide ($CO_2$) (and has an outer diameter of 0.092 inches at the outer wall thereof and an inner diameter of 0.042 inches at the inner wall thereof) and the inner second lumen 574 is circular shaped for the passage of the medical solution of carbon dioxide ($CO_2$) (and has a diameter of 0.030 inches). The inner second lumen 574 is supported within the outer first lumen 572 by first and second radially extending rib members (as shown in FIGS. 7C and 7D) that extend from the outer surface of the second lumen 574 to the inner surface of the outer first lumen 572. In this way the outer first lumen 572 is divided into first and second semicircular passageways 575a, 575b.

The proximal first end 512 of the sintered material tip 528 is formed with a circular recess 550 shaped and dimensioned to correspond with the outlet of the first lumen 572 at the distal end of the dual lumen catheter 560. A longitudinally extending projection 552 extends from the center of the proximal first end 512 and is shaped and dimensioned for frictional placement within the central second lumen 574 so as to close off (with the exception of the porous nature of the sintered material tip) the second lumen 574. The attachment of the sintered material tip 528 at the distal end of the dual lumen catheter 560 is achieved by the provision of a shrink wrap member 554 at the junction of the dual lumen catheter 560 with the sintered material tip 528.

The first lumen 572 and the second lumen 574 are interconnected via the sintered material tip 528 in a manner causing the pressurized medical carbon dioxide ($CO_2$) to effectively pull the medical solution of carbon dioxide ($CO_2$) through the second lumen 574 and into the sintered material tip 528 where they mix to form an enriched medical suspension of carbon dioxide ($CO_2$) and are ultimately forced through the sintered material tip 528. In practice, the medical solution of carbon dioxide ($CO_2$) from syringe 290 travels through the second lumen 574 of the dual lumen catheter 560 and into the sintered material tip 528 when pressurized medical carbon dioxide ($CO_2$) passes through the first lumen 572 and into the sintered material tip 528. The pressurized medical carbon dioxide ($CO_2$) entering the sintered material tip 528 imparts negative pressure on the medical solution of carbon dioxide ($CO_2$) in syringe 290 and draws the medical solution of carbon dioxide ($CO_2$) from the syringe 290 through the second lumen 574 and into the sintered material tip 528. The syringe plunger 290p is used to regulate or stop flow of medical solution of carbon dioxide ($CO_2$) from the syringe 290.

The pressurized medical carbon dioxide ($CO_2$) and medical solution of carbon dioxide ($CO_2$) mixing in the sintered material tip 528 are then forced through the sintered material tip 528 where an enriched medical suspension of carbon dioxide ($CO_2$) forms on the exterior surface 528a of the sintered material tip 528. In particular, the force of the pressurized medical carbon dioxide ($CO_2$) traveling through the Venturi-agitating tip assembly 580 and exiting through the sintered material tip 528 lifts the enriched medical suspension of carbon dioxide ($CO_2$) outward from the exterior surface **528*a* of the sintered material tip 528 and projects the enriched medical suspension of carbon dioxide ($CO_2$) from the second end 580*b* of the Venturi-agitating tip assembly 580**.

In accordance with a fourth embodiment as shown with reference to FIGS. 9A and 9B, a Venturi-agitating tip assembly 680 employs a spray tip 628 in conjunction with a multi-channel arrangement 681 where the pressurized medical carbon dioxide ($CO_2$) and medical solution of carbon dioxide ($CO_2$) are mixed in the Venturi-agitating tip assembly 680 and forced through the spray tip 628. The Venturi-agitating tip assembly 680 includes a proximal first end **680*a* and a distal second end 680*b*. The Venturi-agitating tip assembly 680 includes a cylindrical hollow elongated body 610 having a proximal first end 612, which coincides with the proximal first end 680*a* of the Venturi-agitating tip assembly 680, and a distal second end 614, which coincides with the distal second end 680*b* of the Venturi-agitating tip assembly 680. The Venturi-agitating tip assembly 680 is adapted for use with a dual lumen catheter 660, in particular a dual lumen catheter having concentric lumens, wherein the outer first lumen 672 is annular shaped for the passage of pressurized medical carbon dioxide ($CO_2$) (and has an outer diameter of 0.092 inches at the outer wall thereof and an inner diameter of 0.042 inches at the inner wall thereof) and the inner second lumen 674 is circular shaped for the passage of the medical solution of carbon dioxide ($CO_2$) (and has a diameter of 0.030 inches). The inner second lumen 674 is supported within the outer first lumen 672 by first and second radially extending rib members (as shown in FIGS. 7C and 7D) that extend from the outer surface of the second lumen 674 to the inner surface of the outer first lumen 672. In this way the outer first lumen 672 is divided into first and second semicircular passageways 675*a*, 675*b***.

The proximal first end 612 of the elongated body 610 at the proximal first end **680*a* of the Venturi-agitating tip assembly 680 includes an end wall 661 (created by adhesive injected to limit flow from the first lumen 672) with two projecting channels 662*a*, 662*b* (each with a diameter of 0.015 inches) shaped and dimensioned for engagement with the first and second semicircular passageways 675*a*, 675*b*. The end wall 660 of the proximal first end 612 of the elongated body 610 is also provided with a central aperture 664 shaped and dimensioned for alignment with the second lumen 674. The remainder of the proximal first end 612 of the elongated body 610 is closed off thus limiting and controlling the flow of materials into the central mixing chamber 624**.

The remainder of the Venturi-agitating tip assembly 680 includes a central mixing chamber 624 that is in fluid communication with the second lumen 674 and the two projecting channels **662*a*, 662*b* feeding pressurized medical carbon dioxide ($CO_2$) from the first lumen 672. As a result, and as will be explained below in greater detail the medical solution of carbon dioxide ($CO_2$) and the pressurized medical carbon dioxide ($CO_2$) are mix within the mixing chamber 624 to form an enriched medical suspension of carbon dioxide ($CO_2$). Secured to, and closing off, the second end 614 of the elongated body 610 is a spray tip 628, which is thereby positioned at the distal second end 680*b* of the Venturi-agitating tip assembly 680**.

The first lumen 672 and the second lumen 674 are interconnected in a manner causing the pressurized medical carbon dioxide ($CO_2$) to effectively pull the medical solution of carbon dioxide ($CO_2$) through the second lumen 674 and into the mixing chamber 624. In practice, the medical solution of carbon dioxide ($CO_2$) from the syringe 290 travels through the second lumen 674 of the dual lumen catheter 660 and into the mixing chamber 624 when pressurized medical carbon dioxide ($CO_2$) passes through the first and second projecting channels **662*a*, 662*b* and enters the mixing chamber 624 after being actuated and released from the compressed medical fluid unit 12. The pressurized medical carbon dioxide ($CO_2$) entering the mixing chamber 624 imparts negative pressure on the medical solution of carbon dioxide ($CO_2$) in the syringe 290 and draws the medical solution of carbon dioxide ($CO_2$) from the syringe 290 through second lumen 674 and into the mixing chamber 624. The syringe plunger 290*p* is used to regulate or stop flow of medical solution of carbon dioxide ($CO_2$) from the syringe 290**.

The pressurized medical carbon dioxide ($CO_2$) and medical solution of carbon dioxide ($CO_2$) mixing in the mixing chamber 624 is then forced through the spray tip 628 from which an enriched medical suspension of carbon dioxide ($CO_2$) is sprayed. The force of the pressurized medical carbon dioxide ($CO_2$) traveling through the Venturi-agitating tip assembly 680 and exiting through the spray tip as part of an enriched medical suspension of carbon dioxide ($CO_2$) projects the enriched medical suspension of carbon dioxide ($CO_2$) from the distal second end 684 of the Venturi-agitating tip assembly 680 as a spray and onto the inner lumen of a vessel.

In accordance with a fifth embodiment as shown with reference to FIGS. 10A-10E, a Venturi-agitating tip assembly 780 employs a spray tip 728 in conjunction with a multi-channel arrangement 781 where the pressurized medical carbon dioxide ($CO_2$) and medical solution of carbon dioxide ($CO_2$) are mixed to form an enriched medical suspension of carbon dioxide ($CO_2$) and forced through the spray tip 728. The Venturi-agitating tip assembly 780 includes proximal first end **780*a* and a distal second end 780*b*. The Venturi-agitating tip assembly 780 includes a hollow cylindrical elongated body 710 having a proximal first end 712, which coincides with the proximal first end 780*a* of the Venturi-agitating tip assembly 780, and a distal second end 714. The Venturi-agitating tip assembly 780 is adapted for use with a multi-lumen catheter 760, in particular a triple lumen catheter having parallel lumens, wherein the first and second lumens 772, 773** are circular shaped (each with a diameter of 0.039 inches) and are dimensioned for the passage of pressurized medical carbon dioxide ($CO_2$)

and the third lumen 774 is semi-circular shaped (with a radius of 0.047 inches) and is dimensioned for the passage of the medical solution of carbon dioxide ($CO_2$).

The proximal first end 712 of the elongated body 710 at the proximal first end 780a of the Venturi-agitating tip assembly 780 includes first, second and third inputs 716, 717, 718 for attachment to the multi-lumen catheter 760. The first and second inputs 716, 717 lead to a first channel 720 and the third input 718 to a second channel 722. As such, the proximal first end 712 of the elongated body 710 at the proximal first end 780a of the Venturi-agitating tip assembly 780 is formed with two circular tubular projections 732, 734, defining the first and second inputs 716, 717. The circular tubular projections 732, 734 (each with an inner diameter of 0.027 inches and an outer diameter of 0.039 inches) are shaped and dimensioned for engagement within the first and second lumens 772, 773 of the catheter 760 in a manner allowing for the flow of fluid from the first and second lumens 772, 773 and into the Venturi-agitating tip assembly 780. The two circular tubular projections 732, 734 are shaped and dimensioned to fit within the first and second lumens 772, 773 while maintaining passageways for the passage of pressurized medical carbon dioxide ($CO_2$) therethrough.

The first and second channels 720, 722 lead to, and are in fluid communication with, a mixing chamber 724 located in the central portion 726 of the Venturi-agitating tip assembly 780, that is, between the proximal first end 712 and the distal second end 714 of the elongated body. Secured to the distal second end 714 of the elongated body 710, and positioned at the distal second end 780b of the Venturi-agitating tip assembly, is a spray tip 728 having three passageways 728a, 728b, 728c extending from the mixing chamber 724 to the exterior at the distal end of the Venturi-agitating tip assembly 780.

The first channel 720 and the second channel 722 are interconnected in a manner creating a Venturi effect causing the pressurized medical carbon dioxide ($CO_2$) to effectively pull the medical solution of carbon dioxide ($CO_2$) through the second channel 722 and into the mixing chamber 724. This is achieved by providing the first channel 720 with a reduced diameter (decreasing from 0.038 inches to 0.017 inches) as it extends from the proximal first end 712 of the elongated body 710 (that is, the first end 720a of the first channel 720) to the central portion 726 of the Venturi-agitating tip assembly 780 (that is, the second end 720b of the first channel 720). In accordance with a preferred embodiment, the diameter of the first channel 720 decreases from a diameter of 0.038 inches adjacent the proximal first end 712 of the elongated body 710 to a diameter of 0.017 inches adjacent the mixing chamber 724.

As mentioned above, the second channel 722 is in fluid communication with the first channel 720. This is achieved by the provisional of a transverse channel 730 connecting the second end 720b of the first channel 720 with the second end 722b of the second channel 722. In particular, the second channel 722 includes a first end 722a adjacent the proximal first end 712 of the elongated body 710 and a second end 722b adjacent the mixing chamber 724 (although not directly in fluid communication with the mixing chamber 724) and the transverse channel 730. In accordance with a preferred embodiment, the diameter of the second channel 722 is 0.047 inches and remains consistent as it extends from the first end 722a thereof to the second end 722b thereof.

The first and second lumens 772, 773 supply the pressurized medical carbon dioxide ($CO_2$) and the third lumen 774 supplies the medical solution of carbon dioxide ($CO_2$). As such, the first and second lumens 772, 773 are connected to, and in fluid communication with, the first channel 720 of the Venturi-agitating tip assembly 780 and the third lumen 774 is connected to, and in fluid communication, with the second channel 722 of the Venturi-agitating tip assembly 780. In practice, the medical solution of carbon dioxide ($CO_2$) from syringe 290 travels through third lumen 774 of multi-lumen lumen catheter 760 and into the second channel 722 when pressurized medical carbon dioxide ($CO_2$) gas enters the first channel 720 and passes the transverse channel 730 (having a size of 0.020 inches) into the mixing chamber 724 after being actuated and released from compressed medical fluid unit 12. The pressurized medical carbon dioxide ($CO_2$) entering the Venturi-agitating tip assembly 780 imparts negative pressure on the medical solution of carbon dioxide ($CO_2$) in syringe 290 and draws the medical solution of carbon dioxide ($CO_2$) from the syringe 290 through second channel 722, through the third lumen 774 of the dual lumen catheter 760, and into the mixing chamber 724 due to the Venturi effect. The syringe plunger 290p is used to regulate or stop flow of medical solution of carbon dioxide ($CO_2$) from the syringe 290.

The pressurized medical carbon dioxide ($CO_2$) and medical solution of carbon dioxide ($CO_2$) mixing in the mixing chamber 724 form an enriched medical suspension of carbon dioxide ($CO_2$) that is then forced through the passageways 728a-c of the spray tip 728. The force of the pressurized medical carbon dioxide ($CO_2$) traveling through the Venturi-agitating tip assembly 780 and exiting through the spray tip as part of an enriched medical suspension of carbon dioxide ($CO_2$) projects the enriched medical suspension of carbon dioxide ($CO_2$) from the distal second end 784 of the Venturi-agitating tip assembly 780 as a spray and onto the inner lumen of a vessel.

In accordance with yet another embodiment, the concepts underlying the present invention may be applied in the provision of a medical suspension delivery needle. Such a medical suspension delivery needle would be useful in accessing vessel locations that are inaccessible by the catheter described above. The needle embodiment may also be useful in accessing locations that are limited in length and might not require the use of the suspension delivery catheter described above.

Figure 11A:
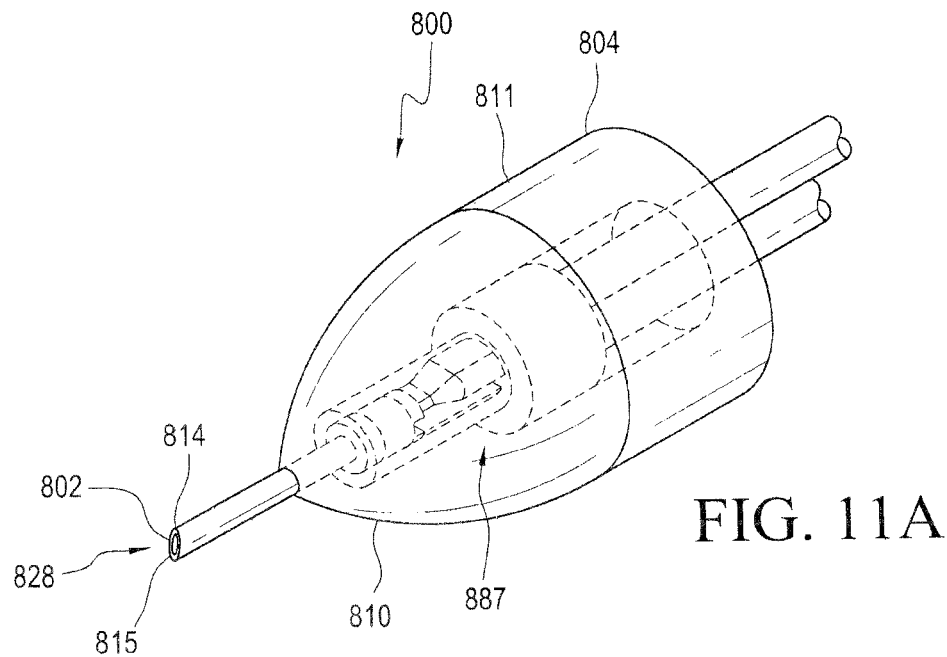
FIGS. 11A and 11B respectively show a perspective view and a cross-sectional view of a Venturi-agitating tip assembly in accordance with the present invention.
Figure 11B:
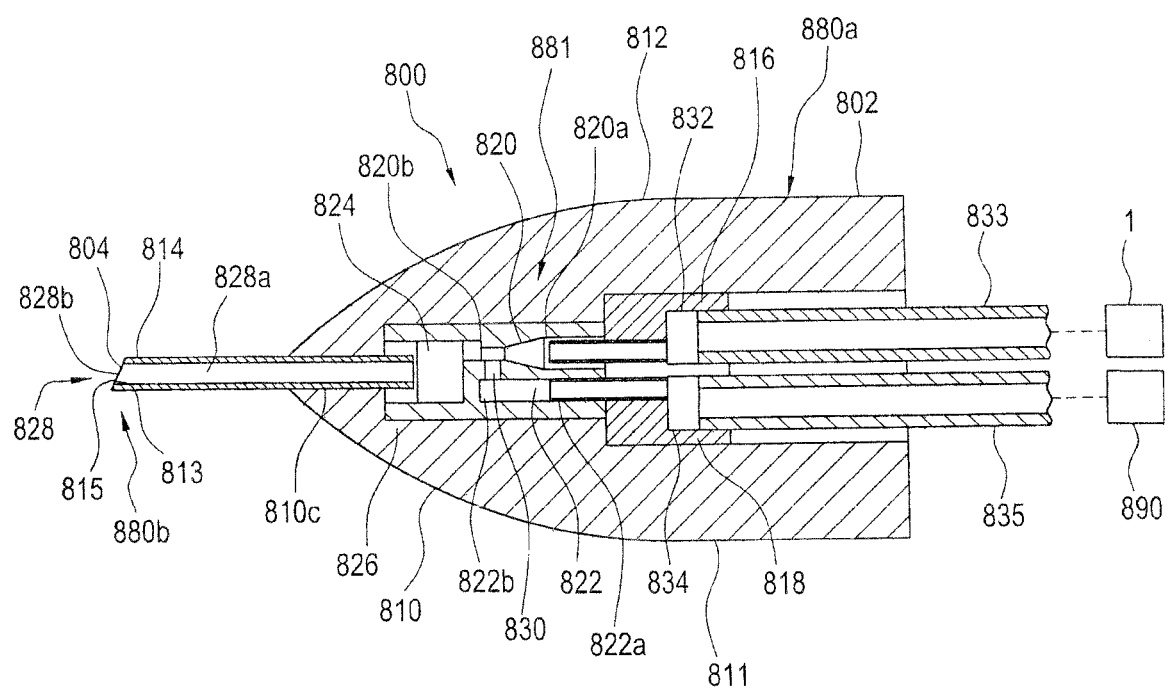

In accordance with such a medical suspension delivery needle embodiment, as shown with reference to FIGS. 11A and 11B, the medical suspension delivery needle 800 has a proximal first end 802, and a distal second end 804. In contrast to the prior embodiments, the medical suspension delivery needle 800 combines the pressurized medical carbon dioxide ($CO_2$) and the medical solution of carbon dioxide ($CO_2$) at the proximal first end 802 of the medical suspension delivery needle 800 and creates an enrich medical fluid suspension of carbon dioxide ($CO_2$) via the inclusion of a porous membrane 815 at the distal second end 804 of the medical suspension delivery needle 800. With this in mind, the medical suspension delivery needle 800 includes a hollow and substantially rigid elongated needle body 810. The needle body 810 includes a needle hub 811 at the proximal first end 812, which coincides with the proximal first end 802 of the medical suspension delivery needle 800, thereof and a sharp beveled edge 813 at the distal second end 814, which coincides with the distal second end 804 of the medical suspension delivery needle 800, thereof. With this in mind, and as will be appreciated based upon the following disclosure, the pressurized medical carbon dioxide ($CO_2$) source (that is, the compressed medical fluid unit 12) and the medical solution of carbon dioxide ($CO_2$) source (that is, the syringe 290) are coupled to respective first and second inputs 816, 818 found within the needle hub 811 at the proximal end 804 of the medical suspension delivery needle 800.

As with the suspension delivery catheters discussed above, the medical suspension delivery needle 800 employs a spray tip 828 in conjunction with a multi-channel arrangement 881 where the pressurized medical carbon dioxide ($CO_2$) and medical solution of carbon dioxide ($CO_2$) are mixed and forced through the spray tip 828 under the force generated by the Venturi system implemented in accordance with the present invention. The Venturi-agitating tip assembly 880 in accordance with the medical suspension delivery needle 800 of the present embodiment includes the spray tip 828 and the multi-channel arrangement 881 that are separated along the length of the needle body 810. However, the Venturi-agitating tip assembly 880 is integrally formed with the needle body 810 and the Venturi-agitating tip assembly 880 is considered to include a proximal first end 880*a* (that coincides with the proximal first end 802 of the suspension delivery needle 800) and a distal second end 880*b* (that coincides with the distal second end 804 of the medical suspension delivery needle 800 and is found in the needle hub 811). As such, the Venturi-agitating tip assembly 880 includes the hollow cylindrical elongated body 810 of the medical suspension delivery needle 800 as well as the internal flow controlling components discussed herein.

As for the needle body 810, and with the exception of the multi-channel arrangement 881 found in the needle hub 811 at the proximal first end 802 of the medical suspension delivery needle 800, it is of a single lumen construction and includes a single lumen cannula 810*c* along that portion distal to the multi-channel arrangement 881 and the hub 811.

The multi-channel arrangement 881 found in the needle hub 811 at the proximal first end 880*a* of the Venturi-agitating tip assembly 880 includes first and second inputs 816, 818 for attachment to the pressurized medical carbon dioxide ($CO_2$) source (that is, the compressed medical fluid unit 12) and the medical solution of carbon dioxide ($CO_2$) (that is, the syringe 290). The first input 816 leads to a first channel 820 and the second input 818 leads to a second channel 822. The proximal first end 880*a* of the Venturi-agitating tip assembly 880, and therefore the proximal first end 812 of the needle body 810, is formed with two circular tubular female coupling recesses 832, 834, defining the first and second inputs 816, 818. The coupling recesses 832, 834 are shaped and dimensioned for fluid coupling with the pressurized medical carbon dioxide ($CO_2$) source (that is, the compressed medical fluid unit 12) and the medical solution of carbon dioxide ($CO_2$) (that is, the syringe 290), for example, via flexible cannulas 833, 835, in a manner allowing for the flow of fluid from the compressed medical fluid unit 12 and the syringe 290), and into the needle body 810.

The first channel 820 leads to, and is in fluid communication with, a mixing chamber 824 located in the central portion 826 of the Venturi-agitating tip assembly 880, that is, between the proximal first end 880*a* and the distal second end 880*b*. Located at the distal second end 880*b* is a spray tip 828 having a passageway 828*a* extending from the mixing chamber 824 to the exterior at the distal end 880*b* of the Venturi-agitating tip assembly 880.

The first channel 820 and the second channel 822 are interconnected in a manner creating a Venturi effect causing the pressurized medical carbon dioxide ($CO_2$) to effectively pull the medical solution of carbon dioxide ($CO_2$) through the second channel 822 and into the mixing chamber 824 where the pressurized medical carbon dioxide ($CO_2$) and the medical solution of carbon dioxide ($CO_2$) mix to form an enriched medical suspension of carbon dioxide ($CO_2$). This is achieved by providing the first channel 820 with a reduced diameter as it extends from the proximal first end 812 of the needle body 810 (that is, the first end 820*a* of the first channel 820) to the central portion 826 of the elongated body 810 (that is, the second end 820*b* of the first channel 820).

As mentioned above, the second channel 822 is in fluid communication with the first channel 820. This is achieved by the provisional of a transverse channel 830 connecting the second end 820*b* of the first channel 820 with the second end 822*b* of the second channel 822. In particular, the second channel 822 includes a first end 822*a* adjacent the proximal first end 812 of the elongated body 810 and a second end 822*b* adjacent the mixing chamber 824 (although not directly in fluid communication with the mixing chamber 824) and the transverse channel 830.

The pressurized medical carbon dioxide ($CO_2$) source supplies the pressurized medical carbon dioxide ($CO_2$) and the medical solution of carbon dioxide ($CO_2$) source supplies the carbon dioxide ($CO_2$). As such, the pressurized medical carbon dioxide ($CO_2$) source is connected to, and in fluid communication with, the first channel 820 of the Venturi-agitating tip assembly 880 and the medical solution of carbon dioxide ($CO_2$) source is connected to, and in fluid communication with, the second channel 822 of the Venturi-agitating tip assembly 880. In practice, a syringe 290 containing medical solution of carbon dioxide ($CO_2$) is secured to the second input 818 at the proximal first end 802 of the suspension delivery needle 800 via a flexible cannula 833 and the pressurized medical carbon dioxide ($CO_2$) from the compressed medical fluid unit 12 is secured to the first input 816 at the proximal first end 802 of the suspension delivery needle 800 via a flexible cannula 835. The medical solution of carbon dioxide ($CO_2$) from the syringe 290 travels through second input 818 and into the second channel 822 when pressurized medical carbon dioxide ($CO_2$) enters the first channel 820 and passes the transverse channel 830 into the mixing chamber 824 after being actuated and released from compressed medical fluid unit 12. The pressurized medical carbon dioxide ($CO_2$) entering the Venturi-agitating tip assembly 880 imparts negative pressure on the medical solution of carbon dioxide ($CO_2$) in syringe 290 and draws the medical solution of carbon dioxide ($CO_2$) from the syringe 290 through second channel 822, through second input 818 of the medical suspension delivery needle 800, and into the mixing chamber 824 due to the Venturi effect. The syringe plunger 290*p* is used to regulate or stop flow from syringe 290.

The pressurized medical carbon dioxide ($CO_2$) and medical solution of carbon dioxide ($CO_2$) mixing in the mixing chamber 824 (to form an enriched medical suspension of carbon dioxide ($CO_2$) are then forced through the remainder of the needle body 810, in particular, the single lumen portion thereof, and through the spray tip 828 from which the enriched medical suspension of carbon dioxide ($CO_2$) is sprayed upon the inner lumen of a vessel. The force of the pressurized medical carbon dioxide ($CO_2$) traveling through the Venturi-agitating tip assembly 880 and exiting through the spray tip as part of an enriched medical suspension of carbon dioxide ($CO_2$) projects the enriched medical suspension of carbon dioxide ($CO_2$) from the distal second end 884 of the Venturi-agitating tip assembly 880 as a spray and onto the inner lumen of a vessel.

It will be appreciated the fluid mechanics of the medical suspension delivery needle embodiment are similar to those of the embodiment discussed with reference to FIGS. 10A-10D, and the dimensions would therefore be similar.

As the medical suspension delivery needle embodiment shows, the concepts underlying the present invention may be implemented using a needle, that is, a rigid cannula, or a catheter, that is, a flexible cannula. Accordingly, the term medical suspension delivery cannula should be considered to encompass both those embodiments implemented using a catheter and those embodiments using a needle.

It is appreciated this procedure can be performed under ultrasound guidance or radiograph in order for the physician to control the amount of liquid to mix with the pressurized medical carbon dioxide ($CO_2$) to form the enriched medical suspension of carbon dioxide ($CO_2$).

The present suspension delivery catheter may be used in the treatment of various vascular ailments. Given that present suspension delivery catheter employs pure $CO_2$ the present suspension delivery catheter is useful in treating arterial ailments as well as treating vascular ailments. As those skilled in the art will appreciate, it is not acceptable to use oxygen for certain procedures within the arterial system given the susceptibility of air embolisms within the arterial system. When using room air or oxygen, the chance of anoxia to the brain, eschemia of the brain, air embolism and stroke are much more prevalent than when using $CO_2$, which very rarely ever causes that type of complication within the venous tree. Also when using room air or oxygen, you cannot use these substances/gases in the arterial tree of the human body. The potential treatments that may employ the present suspension delivery catheter include, but are not limited to the following, microbead delivery in suspension, angiography, stent placement, TIPS (transjugular intrahepatic portosystemic shunt) procedures, magnetic bead delivery, oncology drugs and solutions, etc.

While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

While the preferred embodiments have been shown and described, it will be understood that there is no intent to limit the invention by such disclosure, but rather, it is intended to cover all modifications and alternate constructions falling within the spirit and scope of the invention.

The invention claimed is:

1. An apparatus for creation and delivery of enriched medical suspension, comprising:
   a pressurized gas cylinder containing pressurized medical carbon dioxide ($CO_2$);
   a medical solution of carbon dioxide ($CO_2$);
   a suspension delivery catheter including a dual lumen catheter connecting a Venturi-agitating tip assembly to the pressurized medical carbon dioxide ($CO_2$) and the medical solution of carbon dioxide ($CO_2$), wherein the pressurized medical carbon dioxide ($CO_2$) and the medical solution of carbon dioxide ($CO_2$) are mixed to form an enriched medical suspension.

* * * * *